United States Patent
Fujimoto et al.

(10) Patent No.: US 9,940,715 B2
(45) Date of Patent: Apr. 10, 2018

(54) DIAGNOSIS SUPPORT APPARATUS, METHOD FOR THE SAME, AND NON-TRANSITORY COMPUTER-READABLE STORAGE MEDIUM

(71) Applicant: CANON KABUSHIKI KAISHA, Tokyo (JP)

(72) Inventors: Koji Fujimoto, Kyoto (JP); Masami Kawagishi, Kyoto (JP); Gakuto Aoyama, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 100 days.

(21) Appl. No.: 14/328,609

(22) Filed: Jul. 10, 2014

(65) Prior Publication Data

US 2015/0023579 A1    Jan. 22, 2015

(30) Foreign Application Priority Data

Jul. 17, 2013   (JP) ................................ 2013-148830

(51) Int. Cl.
   *G06K 9/00*   (2006.01)
   *G06T 7/00*   (2017.01)
   *G06F 19/00*  (2018.01)

(52) U.S. Cl.
   CPC .......... *G06T 7/0014* (2013.01); *G06F 19/321* (2013.01); *G06F 19/34* (2013.01); *G06F 19/3487* (2013.01)

(58) Field of Classification Search
   None
   See application file for complete search history.

(56) References Cited

U.S. PATENT DOCUMENTS

2013/0152020 A1*   6/2013   Nishiyama .......... A61B 1/00009
                                                         715/835

FOREIGN PATENT DOCUMENTS

| EP | 2551822 A2 | 1/2013 |
| EP | 2601880 A1 | 6/2013 |
| JP | 2009-271620 A | 11/2009 |
| WO | 2005/122002 A2 | 12/2005 |
| WO | 2012/132840 A1 | 10/2012 |

OTHER PUBLICATIONS

European Search Report issued in corresponding application No. 14176488.6 on Jul. 29, 2015.
Japanese office action issued in corresponding application No. 2013148830 dated May 12, 2017.

(Continued)

*Primary Examiner* — Atiba O Fitzpatrick
(74) *Attorney, Agent, or Firm* — Carter, DeLuca, Farrell & Schmidt, LLP

(57) ABSTRACT

A diagnosis support apparatus obtains a plurality of images as interpretation targets, selects one item of a plurality of image finding items, sequentially assigns evaluations for the selected image finding item to the plurality of images in accordance with an operation input by a user, and displays an image for which an evaluation is assigned, in accordance with the operation input, in a display area, of a plurality of display areas corresponding to evaluations configured to be assigned for the selected image finding item, which corresponds to the evaluation assigned for the image.

19 Claims, 9 Drawing Sheets

(56) References Cited

OTHER PUBLICATIONS

Masahiro Endo et al: "Content-based image-retrieval system in chest computed tomography for a solitary pulmonary nodule: method and preliminary experiments", International Journal of Computer Assisted Radiology and Surgery; A Journal for Interdisciplinary Research, Development and Applications of Image Guided Diagnosis and Therapy, Springer, Berlin, DE, vol. 7, No. 2, Jan. 19, 2012, pp. 331-338.
EP Oral Proceeding summons issued in corresponding application No. 14176488.6 on May 22, 2017.

* cited by examiner

F I G. 1
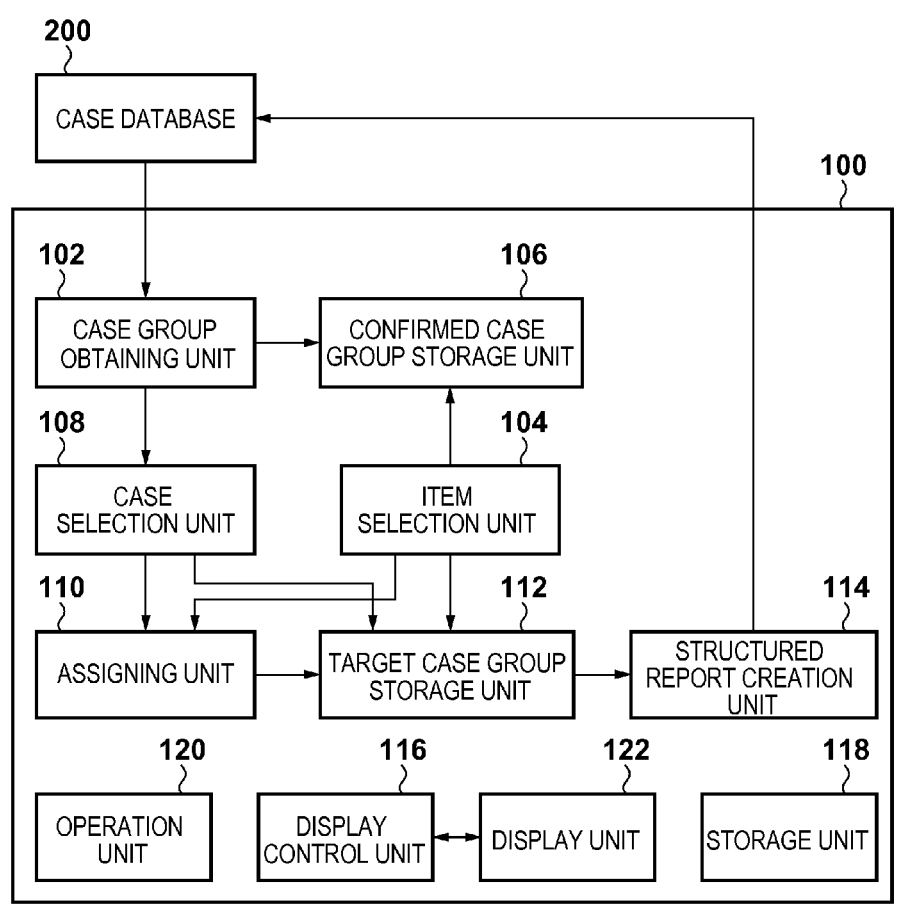

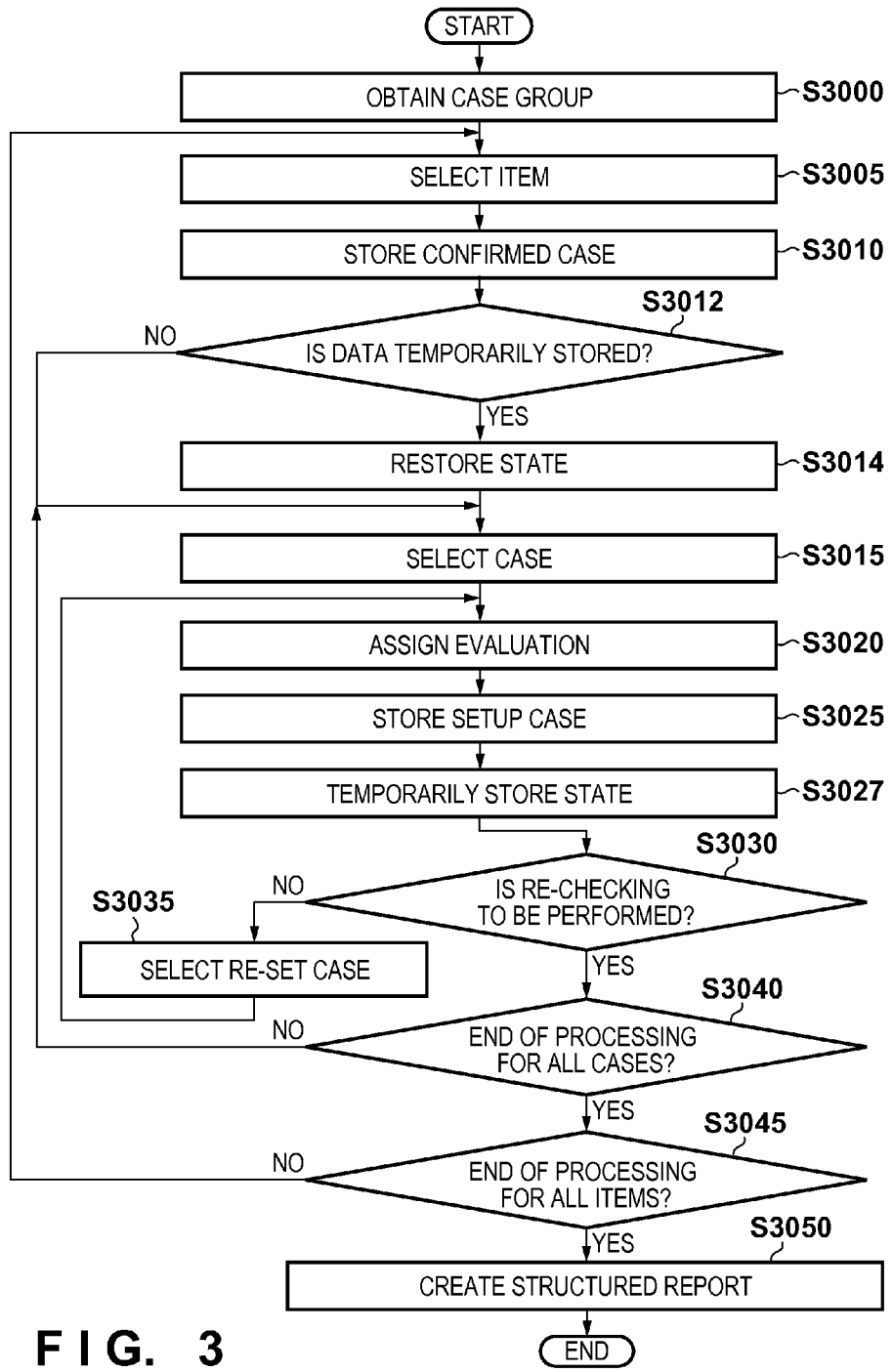
F I G. 3

DIAGNOSIS SUPPORT APPARATUS, METHOD FOR THE SAME, AND NON-TRANSITORY COMPUTER-READABLE STORAGE MEDIUM

BACKGROUND OF THE INVENTION

Field of the Invention

The present invention relates to a diagnosis support apparatus which can collectively perform radiographic interpretation of a plurality of cases while comparing them with each other, a method for the same, and a non-transitory computer-readable storage medium.

Description of the Related Art

In the medical field, doctors perform the imaging diagnosis of performing diagnosis by interpreting the medical images obtained by imaging apparatuses such as an X-ray CT (Computerized Tomography) apparatus and an MRI (Magnetic Resonance Imaging) apparatus. When performing imaging diagnosis, a doctor specifies the symptom of a lesion depicted in an image by comprehensively determining the findings (to be referred to as "image findings" hereinafter) obtained from the image and various kinds of measurement values in accordance with an interpretation request from a primary doctor. The doctor then compiles the process of reaching the diagnosis into an interpretation report to the primary doctor as the request source by using image findings and measurement values.

On the other hand, recently, an attempt has been made to reduce load on a doctor at the time of interpretation report creation by selecting findings and the like in a template form. For example, Japanese Patent Laid-Open No. 2009-271620 discloses a technique of selecting finding elements, phrases, and the like and creating natural sentences. International Publication No. 2005/122002 discloses a technique of analyzing image findings input by a doctor by speech and creating a structured report by using a template and past structured reports.

In general, when performing radiographic interpretation, a doctor creates an interpretation report by performing radiographic interpretation for each case. However, performing radiographic interpretation for each case will produce differences even in similar cases. In such a case, the doctor can perform radiographic interpretation with less differences between cases by collectively performing radiographic interpretation of a plurality of cases while comparing them with each other for each image finding of interest. However, a conventional report creation support apparatus like that disclosed in Japanese Patent Laid-Open No. 2009-271620 is designed to only perform radiographic interpretation for each case but cannot collectively perform radiographic interpretation of a plurality of cases while comparing them with each other.

SUMMARY OF THE INVENTION

In consideration of the above problem, the present invention provides an apparatus which can collectively perform radiographic interpretation of a plurality of cases while comparing them with each other, for each image findings item, so as to perform radiographic interpretation with less differences between cases.

According to one aspect of the present invention, there is provided a diagnosis support apparatus comprising: an obtaining unit configured to obtain a plurality of images as interpretation targets; a selection unit configured to select one item of a plurality of image finding items; a assigning unit configured to sequentially assign evaluations for the selected image finding item to the plurality of images in accordance with an operation input by a user; and a display control unit configured to display an image for which an evaluation is assigned by the assigning unit, in accordance with the operation input, in a display area, of a plurality of display areas corresponding to evaluations configured to be assigned for the selected image finding item, which corresponds to the evaluation assigned for the image.

Further features of the present invention will become apparent from the following description of exemplary embodiments (with reference to the attached drawings).

BRIEF DESCRIPTION OF THE DRAWINGS

FIG. 1 is a block diagram showing the equipment configuration of a diagnosis support apparatus according to the first embodiment;

FIG. 3 is a flowchart showing an overall processing procedure in the first embodiment;

DESCRIPTION OF THE EMBODIMENTS

Figure 2:
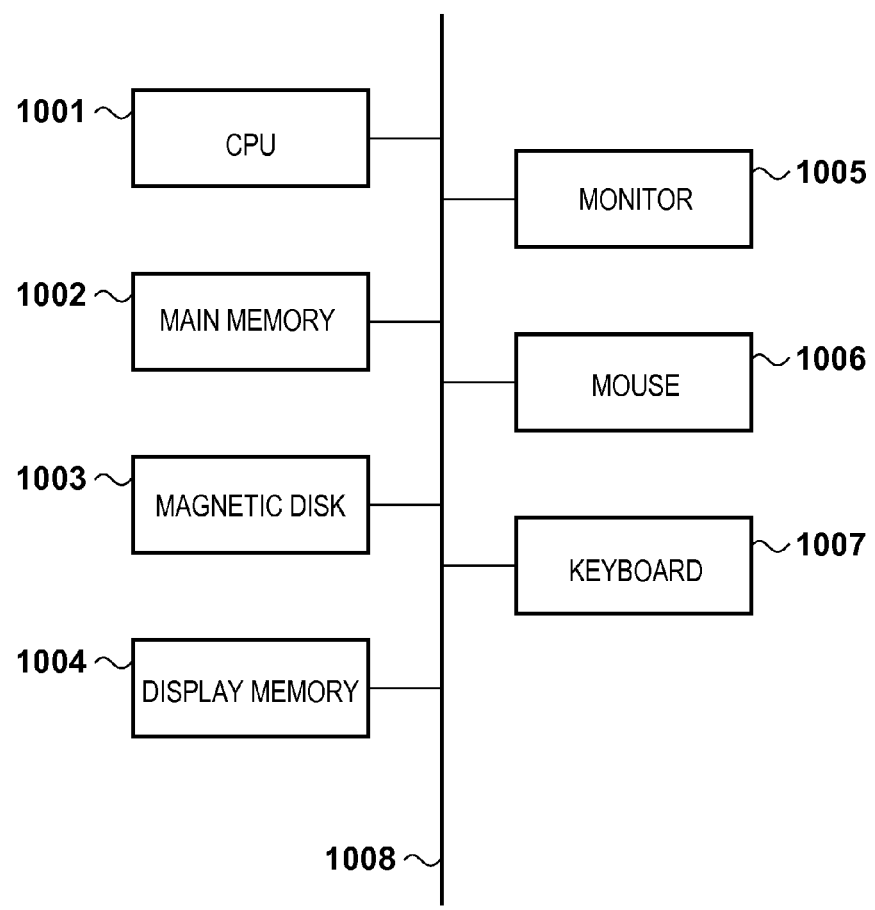
FIG. 2 is a block diagram showing the basic arrangement of a computer which implements each unit of an interpretation report creation support apparatus by software.

A mode (embodiment) for carrying out the present invention will be described below with reference to the accompanying drawings. Note, however, that the scope of the present invention is not limited to that shown in the accompanying drawings.

[First Embodiment]

A diagnosis support apparatus according to this embodiment assigns an evaluation corresponding to each of a plurality of image findings (to be referred to as image finding items hereinafter) with respect to a case as an interpretation target. Note that the following is a case in which the diagnosis support apparatus according to this embodiment is used to assign evaluations corresponding to a plurality of image findings concerning an abnormal shadow in a lung with respect to a plurality of cases and create a structured report. Assume that a medical image to be handled in the following case is chest X-ray CT image, which is constituted by a plurality of tomogram images on transverse planes. Obviously, an interpretation target is not limited to this, and diagnosis names, image findings, and the like are all merely examples for explaining the steps in processing in the diagnosis support apparatus. Assume that the user who uses this apparatus is a doctor.

FIG. 1 shows the arrangement of the diagnosis support apparatus according to the first embodiment. A diagnosis support apparatus 100 according to this embodiment is connected to a case database 200. Assume that the case database 200 is stored in an external server, an external storage device (for example, an FDD, HDD, CD drive, DVD drive, MO drive, or ZIP drive), or the like. The case database 200 stores, as data concerning cases as interpretation targets, medical image information, electronic health record information, and structured reports. If a given case has been interpreted, the structured report created by a structured report creation unit 114 is stored in the case database 200. If a given case has not been interpreted, no corresponding structured report is stored in the case database 200. Note that if a given case has not been interpreted, a structured report explicitly stating that the case has not been interpreted may be stored in the case database 200.

The diagnosis support apparatus 100 includes a case group obtaining unit 102, an item selection unit 104, a confirmed case group storage unit 106, a case selection unit 108, a assigning unit 110, a target case group storage unit 112, the structured report creation unit 114, a display control unit 116, a storage unit 118, an operation unit 120, and a display unit 122. The function of each unit will be described below.

The case group obtaining unit 102 obtains the data group of confirmed (interpreted) cases and the data group of uninterpreted cases, as a case group of an abnormal shadow in a lung as an interpretation target, from the case database 200. The case group obtaining unit 102 then outputs the data group of the confirmed cases to the confirmed case group storage unit 106, and the data group of the uninterpreted cases to the case selection unit 108. The item selection unit 104 selects one of a plurality of image finding items corresponding to the interpretation target (that is, the abnormal shadow in the lung) according to the operation by the user. The item selection unit 104 outputs the selected image finding item to the confirmed case group storage unit 106, the assigning unit 110, and the target case group storage unit 112. In this case, if an image finding item is selected by the item selection unit 104, a plurality of evaluations are specified, which can be assigned with respect to the selected image finding item.

The confirmed case group storage unit 106 stores the data of the confirmed cases obtained by the case group obtaining unit 102 while dividing the data according to the plurality of evaluations corresponding to the image finding item selected by the item selection unit 104. More specifically, the confirmed case group storage unit 106 checks evaluations corresponding to the image finding item selected by the item selection unit 104 with respect to each confirmed case by referring to the structured report stored in the case database 200. The confirmed case group storage unit 106 then stores, based on the checked evaluations, the respective data of the confirmed cases for the respective evaluations.

The case selection unit 108 selects, by the user operation, the data of one case of the data group of the uninterpreted cases obtained by the case group obtaining unit 102. The case selection unit 108 outputs the data of the selected case to the assigning unit 110 and the target case group storage unit 112. The assigning unit 110 sequentially assigns, by the user operation, one of a plurality of evaluations which can be assigned for the image finding item selected by the item selection unit 104, with respect to the case selected by the case selection unit 108. The assigning unit 110 outputs the assigned evaluation to the target case group storage unit 112. The target case group storage unit 112 stores the data of the case selected by the case selection unit 108, based on the evaluations assigned by the assigning unit 110 which are evaluations corresponding to the image finding item selected by the item selection unit 104.

The structured report creation unit 114 creates a structured report based on the evaluations corresponding to each image finding item stored in the target case group storage unit 112. The structured report creation unit 114 outputs the created structured report to the case database 200 and stores the report. The display control unit 116 controls display on a display unit (not shown) in accordance with the operation of each unit of the diagnosis support apparatus 100. This control will be described in detail later.

The operation unit 120 accepts an operation input from the user and outputs a signal corresponding to the operation input to the diagnosis support apparatus 100. The operation unit 120 includes, for example, a plurality of buttons and a pointing device, and implements the operation of an icon or image on a display screen displayed on the display unit 122. In addition, the operation unit 120 is one or a combination of a touch panel device integrally formed with the display unit 122, a mouse device, and a keyboard. When, for example, the user performs an input operation by touching a medical image on the display screen with the touch panel device, the diagnosis support apparatus 100 sets the image in a selected state according to a signal corresponding to the operation input. Alternatively, the medical image is set in a selected state by moving the cursor on the display screen to the medical image with the mouse device and clicking a button. In addition, the diagnosis support apparatus 100 updates the positional coordinates of the medical image by performing the input operation of moving the touched position while keeping the touched state. The display control unit 116 then implements display control to move the selected medical image on the screen. Alternatively, the same display control is also implemented by the so-called drag & drop operation of moving the cursor while pressing a button of the mouse.

Note that at least some of the units of the diagnosis support apparatus 100 shown in FIG. 1 may be implemented as independent devices. Alternatively, each unit may be implemented as software which implements a corresponding function. Assume that in this embodiment, each unit is implemented by software.

FIG. 2 is a block diagram showing the basic arrangement of a computer for implementing the function of each unit shown in FIG. 1 by executing software. A CPU 1001 mainly controls the operation of each constituent element. A main memory 1002 stores control programs to be executed by the CPU 1001 and provides a work area at the time of execution of a program by the CPU 1001. A magnetic disk 1003 stores an OS (Operating System), device drivers of peripheral devices, various types of application software including programs for performing processing and the like (to be described later), and the like.

A display memory 1004 temporarily stores display data. A monitor 1005 is, for example, a CRT monitor or liquid crystal monitor, which displays images and texts based on data from the display memory 1004. The user performs a pointing input operation and inputs characters and the like by using a mouse 1006 and a keyboard 1007. Note that the monitor 1005 corresponds to the display unit 122 in FIG. 1, and the mouse 1006 and the keyboard 1007 correspond to the operation unit 120 in FIG. 1. In addition, the respective constituent elements described above are communicatively connected to each other via a common bus 1008.

Figure 4:
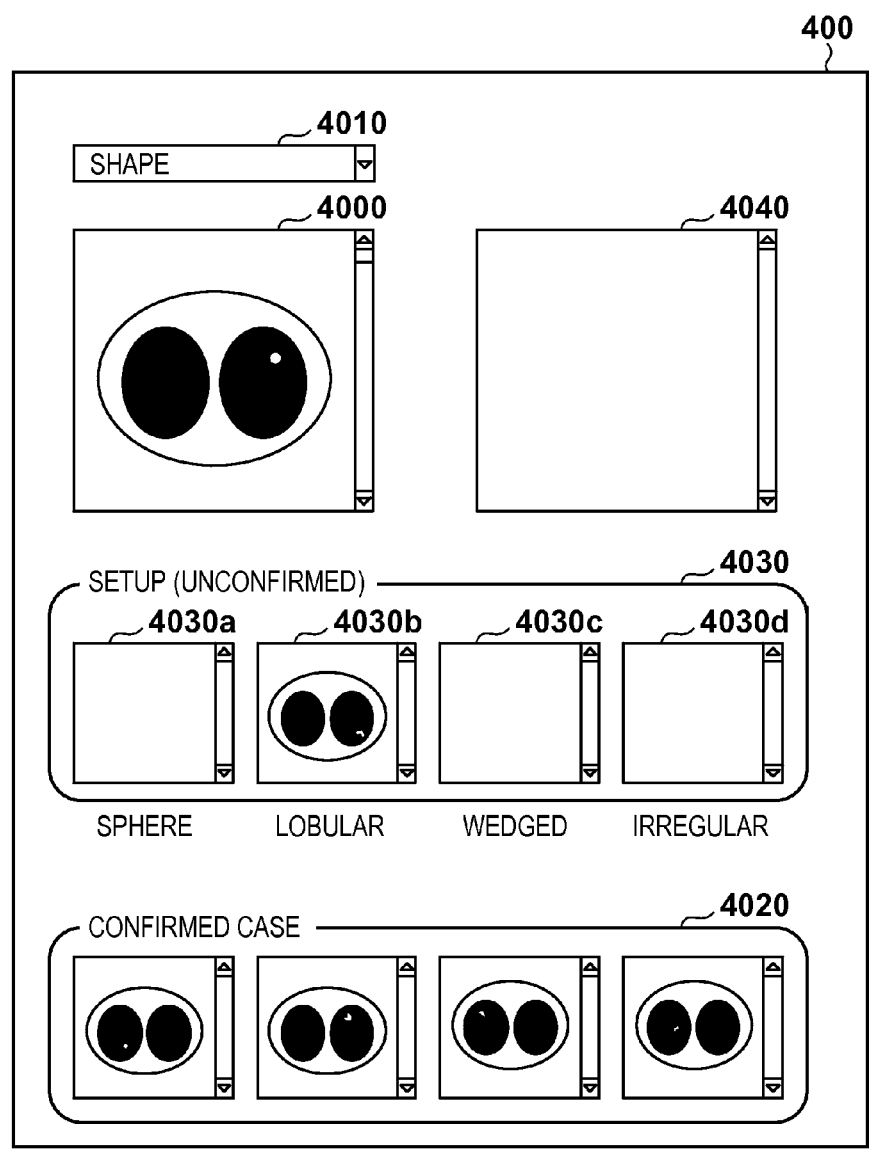
FIG. 4 is a view showing an example of a GUI in the first embodiment.

Overall processing performed by the diagnosis support apparatus 100 will be described with reference to FIGS. 3 and 4. FIG. 3 is a flowchart showing an overall processing procedure in this embodiment. FIG. 4 is a view showing an example of a GUI 400 in this embodiment. In the embodiment, referring to FIG. 3, the CPU 1001 executes programs stored in the main memory 1002 to implement the functions of the respective units. Assume that the user operates the GUI 400 in FIG. 4 to perform processing in the item selection unit 104, the case selection unit 108, and the assigning unit 110. Obviously, an operation using the GUI 400 is merely an example of processing, and the GUI 400 in FIG. 4 is an example. Note that a target case list 4000, a confirmed case area 4020, a assigned case area 4030, an evacuation case list 4040, and the like each are an example of a display object. However, the present invention is not limited to them.

In step S3000, the case group obtaining unit 102 obtains the data group of confirmed (interpreted) cases and the data group of uninterpreted cases concerning the abnormal shadow in the lung from the case database 200. More specifically, the case group obtaining unit 102 refers to the case database to determine, as an uninterpreted case, a case without a structured report corresponding to a medical image or with a structured report explicitly stating that the case has not been interpreted. On the other hand, the case group obtaining unit 102 refers to the case database to determine a case with a structured report as a confirmed case. The case group obtaining unit 102 obtains the data group of uninterpreted cases and the data group of confirmed cases from the case database 200 by using this determination result.

In this embodiment, the display control unit 116 displays the data group of uninterpreted cases obtained by the case group obtaining unit 102 in the target case list 4000 of the GUI 400 in FIG. 4. Note that in this embodiment, as shown in FIG. 4, a list of representative images of medical images corresponding to each case of an uninterpreted case group is displayed as the target case list 4000. However, a list of case IDs may be displayed. In this case, it is possible to use, as a representative image, a tomogram image, of tomogram images on a plurality of transverse planes (to be described later), which exhibits the highest likelihood of an abnormal shadow which can be detected by using an abnormal shadow detection unit (not shown).

Figure 8:
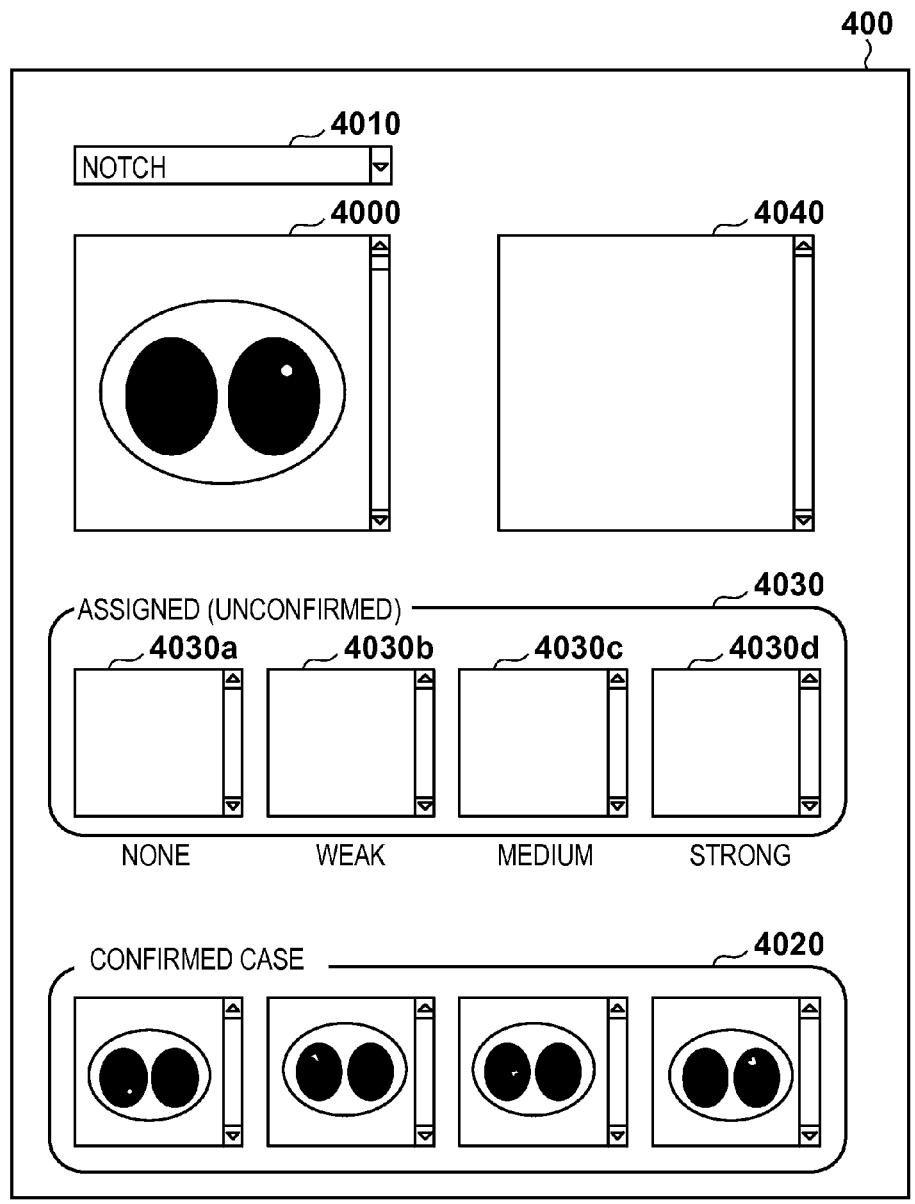
FIG. 8 is a view showing another example of a GUI in the first embodiment.

In step S3005, the item selection unit 104 selects one of a plurality of image finding items concerning the abnormal shadow in the lung. This operation is implemented when the user selects an image finding item from an image finding item list 4010 of the GUI 400 in FIG. 4. The image finding item list 4010 contains an image finding item "shape" indicating the overall shape of an abnormal shadow and an image finding item "notch" indicating whether there is Notch Sign on the contour of the shadow. This "shape" is evaluated by, for example, four values, namely "sphere", "lobular", "wedged", and "irregular", as indicated by display areas 4030*a* to 4030*d* in FIG. 4. Likewise, with regard to an image finding item "lobular", as shown in FIG. 8, for example, the intensity of Notch Sign is evaluated by four discrete values, namely "none", "weak", "medium", and "strong".

The display areas 4030*a* to 4030*d* will be described below. The display areas 4030*a*, 4030*b*, 4030*c*, and 4030*d* are display areas respectively corresponding to a plurality of evaluations corresponding to a selected image finding item. In the example shown in FIG. 4, the display areas 4030*a* to 4030*d* are displayed side by side, which correspond to the respective evaluation items of "sphere", "lobular", "wedged", and "irregular" concerning the image finding item "shape". In this case, the display control unit 116 displays a medical image whose evaluation is assigned by the assigning unit 110 in a display area corresponding to the evaluation.

In the example shown in FIG. 4, each of the display areas 4030*a* to 4030*d* allows only one medical image to be displayed at once. It is possible to switch an image to be displayed in accordance with the input operation of pressing an upper triangle button "A" and an inverted triangle button "V" on the right side of each display area. This allows the user to easily grasp, from the medical image displayed in each display area, the correspondence relationship between the evaluation and the image. This also facilitates re-checking the evaluation assignment for a medical image after the evaluation is assigned.

In addition, in another embodiment, each display area may display a plurality of images to compare the plurality of images for which similar evaluations are assigned, upon arranging the images side by side. This leads to an improvement in the accuracy of evaluation assigning by the user.

In still another embodiment, a display area may not be divided into display areas 4030*a* to 4030*d*, and only a assigned case area 4030 may exist. In this case, the position of the assigned case area 4030 corresponds to an evaluation value. For example, the upper left position of a medical image moved into the assigned case area 4030 corresponds to the evaluation value in a selected image finding item. In this case, "a display area corresponding to an assigned evaluation" exists by the number of display pixels of the assigned case area 4030. Obviously, a common evaluation may be given at a plurality of pixel positions.

In step S3010, the confirmed case group storage unit 106 stores the data of the confirmed cases, obtained by the case group obtaining unit 102 in step S3000, for the respective evaluations corresponding to the image finding item selected by the item selection unit 104 in step S3005. If, for example, the image finding item selected in step S3005 is "shape", the confirmed case group storage unit 106 checks a structured report corresponding to each confirmed case, and checks the evaluation of "shape" corresponding to each case. The confirmed case group storage unit 106 then stores the data of the confirmed cases respectively for the four evaluations, namely "sphere", "lobular", "wedged", and "irregular", as evaluations which can be assigned for "shape". In this embodiment, the display control unit 116 displays the stored data of the confirmed cases in the confirmed case area 4020 shown in FIG. 4 as a list of representative images like the target case list 4000 in step S3000.

In step S3012, the diagnosis support apparatus 100 checks whether data linked to the image finding item selected by the item selection unit 104 in step S3005 is stored in the storage unit 118. If there is linked data (YES in step S3012), the process advances to step S3014. In step S3014, the diagnosis support apparatus 100 reads out the data linked to the image finding item selected by the item selection unit 104 in step S3005 from the storage unit 118, and restores the state of the data (step S3014). The stored data and restoration will be described in detail with reference to step S3027.

When the state of the data is restored (step S3014) and there is no linked data (NO in step S3012), the process advances to step S3015. In step S3015, the case selection unit 108 selects, by the user operation, the data of one case of the data group of the uninterpreted cases obtained in step S3000. This operation is implemented when, for example, the user selects a case from the target case list 4000 of the GUI 400 in FIG. 4. In this case, when the user selects one case from the target case list 4000, a medical image viewer (not shown) starts. This makes it possible to closely examine a medical image corresponding to the selected case. Note that a viewer activation unit (not shown) may be used to activate this medical image viewer.

Processing in the medical image viewer will be briefly described below. In this embodiment, when the medical image viewer is activated, the above representative image is displayed as an initial state in an image display area. The user closely examines the medical image while moving (changing the tomogram image to be displayed) the tomogram image forward and backward (to the head side and the tail side) by operating the mouse. In addition, a viewer control unit (not shown) enlarges/reduces a tomogram image, translates the display position, and changes the gray level contrast in the image display area of the viewer based on the operation by the user. Furthermore, this viewer control unit reconstructs a slice in an arbitrary direction from the above tomogram image and displays the reconstructed image on the viewer based on the operation by the user. This operation is called arbitrary slice reconstruction, which can reconstruct an image on a slice in an arbitrary direction. In general, however, an image on a plane (coronal plane or sagittal plane) perpendicular to a transverse plane is often reconstructed.

Figure 5:
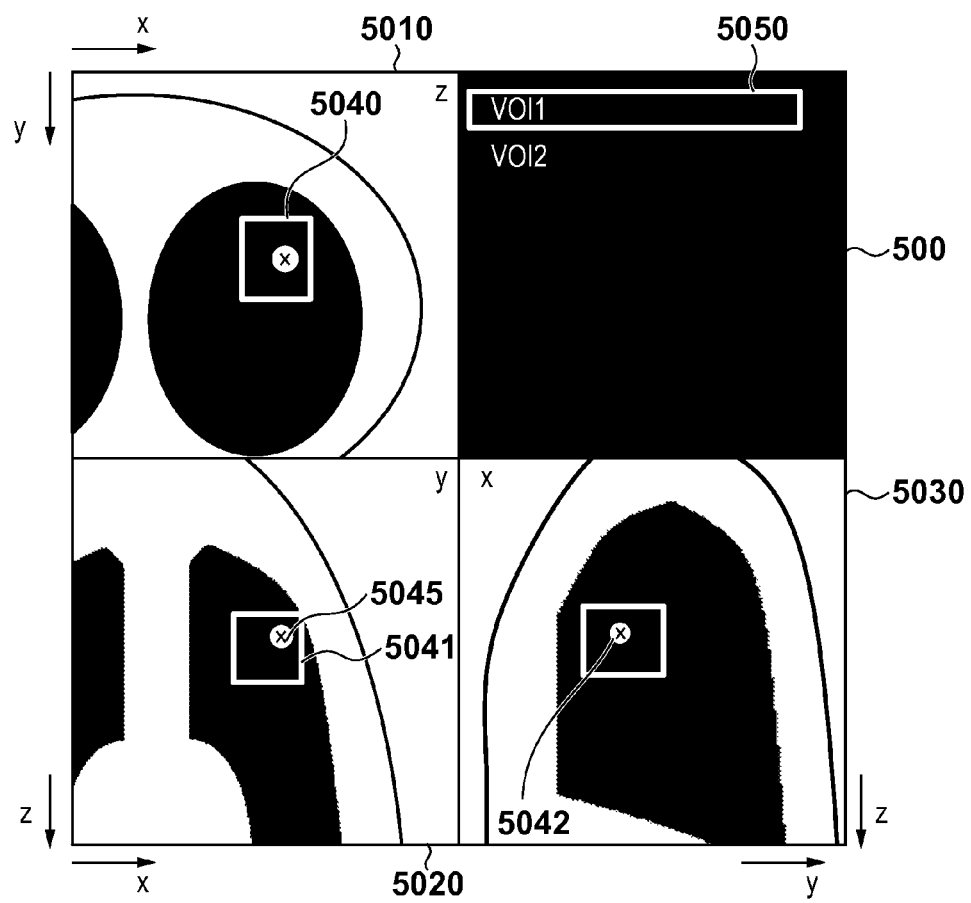
FIG. 5 is a view showing an example of a medical image viewer in the first embodiment.

A tomogram image on a transverse plane, a tomogram image on a coronal plane, and a tomogram image on a sagittal plane will be respectively referred to as an axial image, a coronal image, and a sagittal image hereinafter. In addition, in the following description, x-, y-, and z-axes are set such that an axial image, a coronal image, and a sagittal image respectively become an x-y plane image, an x-z plane image, and a y-z plane image. That is, the body axis direction, the lateral direction of the body, and the anteroposterior direction of the body are respectively defined as the z-axis, the x-axis, and the y-axis. In this case, simultaneously and synchronously displaying an axial image, a coronal image, and a sagittal image will be referred to as MPR (Multi-Planar Reconstruction) display. FIG. 5 shows an example of performing MPR display by using the image viewer according to this embodiment. FIG. 5 is a view showing an example of the medical image viewer in the embodiment. FIG. 5 shows an axial image 5010, a coronal image 5020, and a sagittal image 5030.

Assume that in this embodiment, the user mainly performs close examination by MPR display. When the user finds an abnormal shadow, he/she designates a region surrounding the abnormal shadow as a region of interest in the form of a rectangular parallelepiped. This rectangular parallelepiped will be referred to as a VOI (Volume Of Interest) hereinafter. More specifically, a VOI is designated by setting rectangles whose coordinates are synchronized on an axial image, a coronal image, and a sagittal image. These rectangles have the following relationship:

longitudinal axis of rectangle 5040 of axial image 5010=transverse axis of rectangle 5042 of sagittal image 5030 transverse axis of rectangle 5040 of axial image 5010=transverse axis of rectangle 5041 of coronal image 5020 longitudinal axis of rectangle 5041 of coronal image 5020=longitudinal axis of rectangle 5042 of sagittal image 5030

In this embodiment, first of all, the user designates an attention point 5045 on any one of an axial image, a coronal image, and a sagittal image. When the user designates the attention point 5045 on any one of the images, the coordinate position (x, y, z) of the designated position is uniquely confirmed. In this case, when the user designates the attention point 5045, the viewer control unit displays the attention point 5045 on the viewer such that the point is located in the central portion of each of the axial image, the coronal image, and the sagittal image.

For example, when the user designates an attention point on an axial image, the tomogram positions of sagittal and coronal images to be displayed are determined from the x- and y-coordinates of the attention point and a z-coordinate corresponding to the tomogram position of the axial image. The viewer control unit displays the attention point 5045, based on the (y, z) coordinates and (x, z) coordinates of the attention point designated on the axial image, so as to locate the attention point 5045 in the central portion of each of the sagittal and coronal images. Note, however, that when the attention point is displayed in the central portion of each tomogram image, a tomogram image is not sometimes displayed in the overall image display area. This will be described with reference to FIGS. 6A to 6D.

Figure 6:
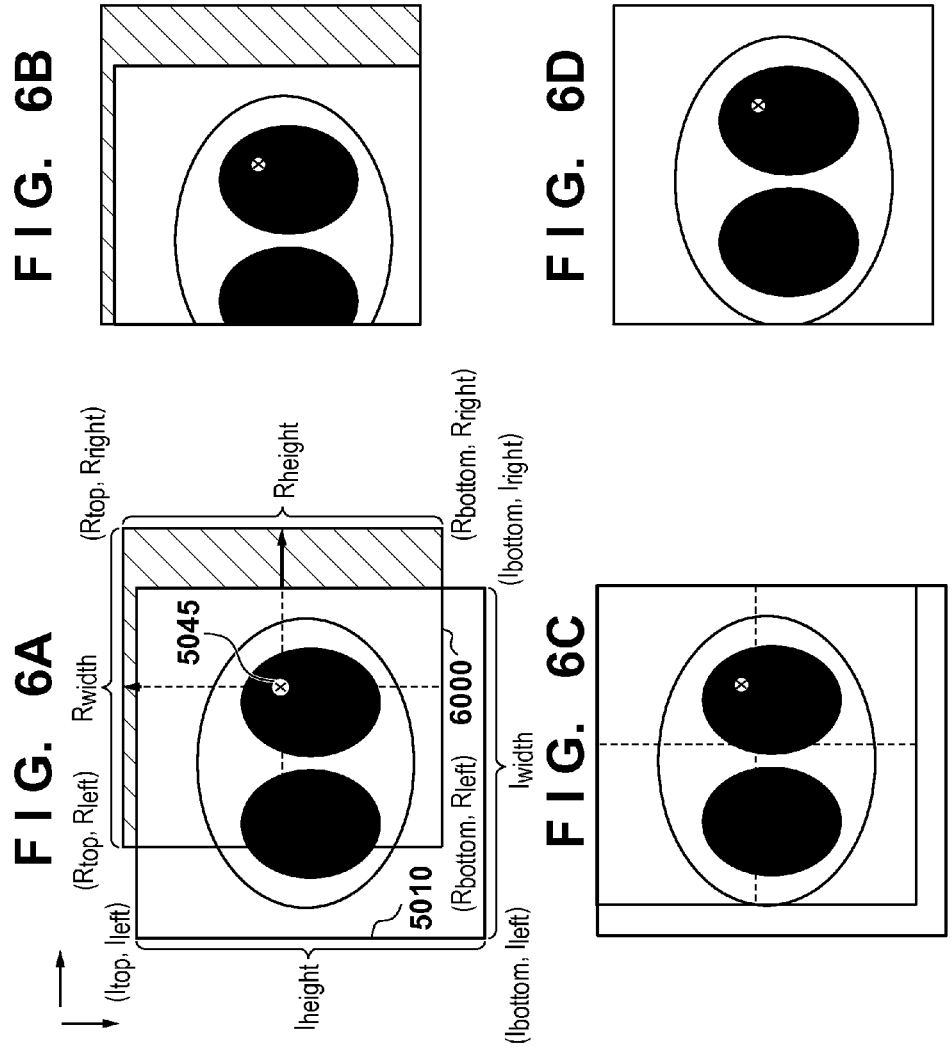
FIGS. 6A to 6D are views each showing a display example of a tomogram image in the first embodiment.

FIGS. 6A to 6D are views each showing a display example of a tomogram image (axial image 5010) in this embodiment. FIG. 6A shows an example in which a tomogram image is not entirely displayed in an image display area 6000 because an attention point on a tomogram image is displayed so as to be located in the center of the image display area 6000. As a result, the image is displayed on the GUI 400, as shown in FIG. 6B. In order to prevent this, the display control unit 116 performs the following processing so as to entirely display the tomogram image in the image display area.

First of all, the display control unit 116 obtains a size $I_{height}$ of a tomogram image in the longitudinal axis direction and a size $R_{height}$ of the image display area 6000 in the longitudinal axis direction, and compares $I_{height}$ with $R_{height}$. If $I_{height}$ is smaller than $R_{height}$, the tomogram image does not entirely cover the image display area 6000 in the longitudinal axis direction regardless of how the tomogram image is placed in the longitudinal axis direction. In such a case, the tomogram image is displayed such that its midpoint in the longitudinal axis direction coincides with the midpoint of the image display area 6000 in the longitudinal axis direction. In contrast, if $I_{height}$ is equal to or more than $R_{height}$, the display control unit 116 obtains coordinates $I_{top}$ and $I_{bottom}$ of a vertex of the tomogram image in the longitudinal axis direction and coordinates $R_{top}$ and $R_{bottom}$ of a vertex of the image display area 6000 in the longitudinal axis direction.

In this case, when $I_{top}$ is larger than $R_{top}$, it indicates that $I_{top}$ is located below $R_{top}$ in the longitudinal axis direction, and the tomogram image is not displayed on the upper side of the image display area 6000. In this case, in order to prevent this state, $I_{top}$ is translated to coincide with $R_{top}$. At this time, since $I_{height}$ is larger than $R_{height}$, the tomogram image is displayed in the overall image display area 6000 in the longitudinal axis direction.

On the other hand, if $I_{bottom}$ is smaller than $R_{bottom}$, it indicates that $I_{bottom}$ is located above $R_{bottom}$ in the longitudinal axis direction, and the tomogram image is not displayed on the lower side of the image display area 6000. In this case, in order to prevent this state, $I_{bottom}$ is translated to coincide with $R_{bottom}$. At this time, since $I_{height}$ is larger than $R_{height}$, the tomogram image is displayed in the overall image display area 6000 in the longitudinal axis direction.

If $I_{top}$ is equal to or less than $R_{top}$ and $I_{bottom}$ is equal to or more than $R_{bottom}$, since the tomogram image is entirely displayed in the image display area 6000 in the longitudinal axis direction, the above translation is not performed. The processing described above concerning the longitudinal axis direction is applied to the transverse axis direction. In this case, it is necessary to read longitudinal as transverse, up and down as left and right, and height as width. Performing processing in both the longitudinal axis direction and the transverse axis direction will properly translate the tomogram image. As a consequence, as shown in FIGS. 6C and 6D, the tomogram image is properly displayed in the image display area 6000.

The viewer control unit performs the above processing for an axial image, a coronal image, and a sagittal image, thereby properly displaying the images on all the slices. Note that the processing of properly displaying images can be applied to a case in which an image is enlarged or reduced on an arbitrary slice.

A rectangle indicating a VOI is then set on each of the axial image, the coronal image, and the sagittal image. When setting this rectangle, however, the rectangle is set so as to contain the attention point 5045 without fail. It is possible to implement this processing by a method such as determining whether the attention point 5045 exists in the set rectangle and, if it is determined that the attention point 5045 does not exist, invalidating the set rectangle and setting a rectangle again.

In this embodiment, when the user sets a VOI, the viewer control unit stores the size of the VOI and the coordinates of the attention point 5045 in a VOI list 5050. Note that it is possible to set a plurality of VOIs for one case. In this case, when the user selects a VOI set in the VOI list 5050, the viewer control unit displays each tomogram image on the viewer based on the stored size of the VOI and the stored attention point 5045. In this case, as described above, the viewer control unit displays the axial image 5010, the coronal image 5020, and the sagittal image 5030 such that the attention point 5045 is located in the central portion of each image. Note that the above processing may be expanded to display a rectangle indicating a VOI in the image display area 6000 without fail. In addition, processing such as image processing may be performed by using the set VOI and the attention point 5045. For example, it is possible to perform area extraction processing by using a method such as a graph cut method using the attention point 5045 as a seed point.

In step S3020, the assigning unit 110 assigns an evaluation for an image finding item corresponding to the case based on the image finding item selected in step S3005 and the case selected in step S3015. For example, this operation is implemented when the user inputs the first image displayed at the movement source into a corresponding area at the movement destination. More specifically, the operation is implemented when the user operates the operation unit 120 to drag & drop a representative image displayed in the target case list 4000 shown in FIG. 4 to an area corresponding to the evaluation in the assigned case area 4030.

Consider, for example, a case in which the image finding item selected in step S3010 is "shape", and "sphere" is selected as an evaluation in step S3020 as a result of closely examining the medical image of the case. In this case, the user may drag & and drop the selected representative image of the medical images (that is, the image displayed in the target case list 4000) to a corresponding area (that is, the leftmost area in FIG. 4) in the assigned case area 4030. Likewise, if an evaluation is "irregular", the user may drag & drop the image to the rightmost area.

At this time, the user may perform radiographic interpretation while comparing lists as references for the respective evaluations in the confirmed case area 4020. Likewise, the user may perform radiographic interpretation while comparing lists as references for the respective evaluations in the assigned case area 4030, as will be described with reference to step S3025. Although comparison may be performed based on representative images, other methods may be used. If the user is unsure about his/her determination, he/she may drag & drop an image to the evacuation case list 4040 and perform determination later. The evacuation case list 4040 is also managed in the same manner as the target case list 4000. In this case, the display control unit 116 displays images as a list of representative images in the evacuation case list 4040 shown in FIG. 4 like the target case list 4000 in step S3000.

In step S3025, the target case group storage unit 112 stores, based on the evaluation assigned in step S3020, the data of the case selected in step S3015 for each of a plurality of evaluations corresponding to the image finding item selected in step S3005. Assume that the image finding item selected in step S3005 is "shape", and the evaluation assigned in step S3020 is "sphere". In this case, the data of the case selected in step S3015 is stored in addition to the evaluation "sphere". In this embodiment, the display control unit 116 displays the stored data of the assigned case as a list of representative images for each evaluation in the assigned case area 4030 shown in FIG. 4 like the target case list 4000 in step S3000.

Note that when the data is added to the list of representative images, the data may be added to the head or tail of the list at the movement destination. When the user performs drag & and drop, it is possible that the target case list 4000 automatically displays a representative image (second image) of the next case. In this case, the representative image at the head of the list can be displayed. In addition, a representative image of the case at the movement source may be displayed when the user moves the selected case by dragging operation.

In step S3027, the storage unit 118 stores the current state while linking it to the image finding item selected in step S3005. More specifically, the storage unit 118 stores the target case list 4000, a list for each evaluation in the confirmed case area 4020, a list for each evaluation in the assigned case area 4030, and the evacuation case list 4040. In addition, the storage unit 118 stores a representative image of each list displayed by the display control unit 116. This stored state is reproduced in step S3014. That is, the storage unit 118 stores information stored in the target case list 4000, the list for each evaluation in the confirmed case area 4020, the list for each evaluation in the assigned case area 4030, and the evacuation case list 4040. The display control unit 116 then displays a representative image of each list.

In step S3030, the diagnosis support apparatus 100 determines whether the evaluation assigned for each interpreted case is to be rechecked. In general, the doctor performs this determination. If the doctor determines to perform rechecking, the process advances to step S3035. If the doctor determines not to perform rechecking, the process advances to step S3040.

In step S3035, the case selection unit 108 selects the data of one case of the data group of uninterpreted cases stored in the target case storage unit by the processing in step S3025. Alternatively, as a result of the processing in step S3020, the data of one case of the data group of uninterpreted cases managed by the evacuation case list 4040 is selected. This operation is implemented when the user selects a case to be re-set from the assigned case area 4030 or the evacuation case list 4040 shown in FIG. 4. After the selection, the process advances to step S3020 to execute the processing in steps S3020 to S3030 described above. Note that this processing differs from the processing in steps S3020 to S3030 described above in that the selected case is the case selected in step S3035.

This processing will be described with reference to a concrete example. Consider a case in which the case assigned as "sphere" in step S3020 needs to be re-set to "irregular". In this case, the user may select a corresponding case from the leftmost area (that is, the assigned case group set as "sphere") in the assigned case area 4030 and drag & drop the selected case to the rightmost area.

In step S3040, the diagnosis support apparatus 100 determines whether there is any case, among all the interpretation target cases, for which any evaluation for the image finding item selected in step S3005 has not been set. Note that in this embodiment, when the target case list 4000 and the evacuation case list 4040 in FIG. 4 simultaneously become empty, it is determined that evaluations have been set for all the cases. In this case, if it is determined that evaluations have been set for all the cases, the process advances to step S3045. If it is determined that there is any case for which any evaluation has not been set, the process advances to step S3015 to execute the processing in steps S3015 to S3035.

In step S3045, the diagnosis support apparatus 100 determines whether all image finding items have been set. Note that in this embodiment, in step S3045, the image finding item selected in step S3005 is erased from the image finding item list 4010 in FIG. 4. In this case, if the image finding item list becomes empty, it is determined that all the image finding items have been set. In this case, if it is determined that all the image finding items have been set, the process advances to step S3050. If there is any image finding item which has not been set, the process advances to step S3005 to execute the processing in steps S3005 to S3040.

Figure 7:
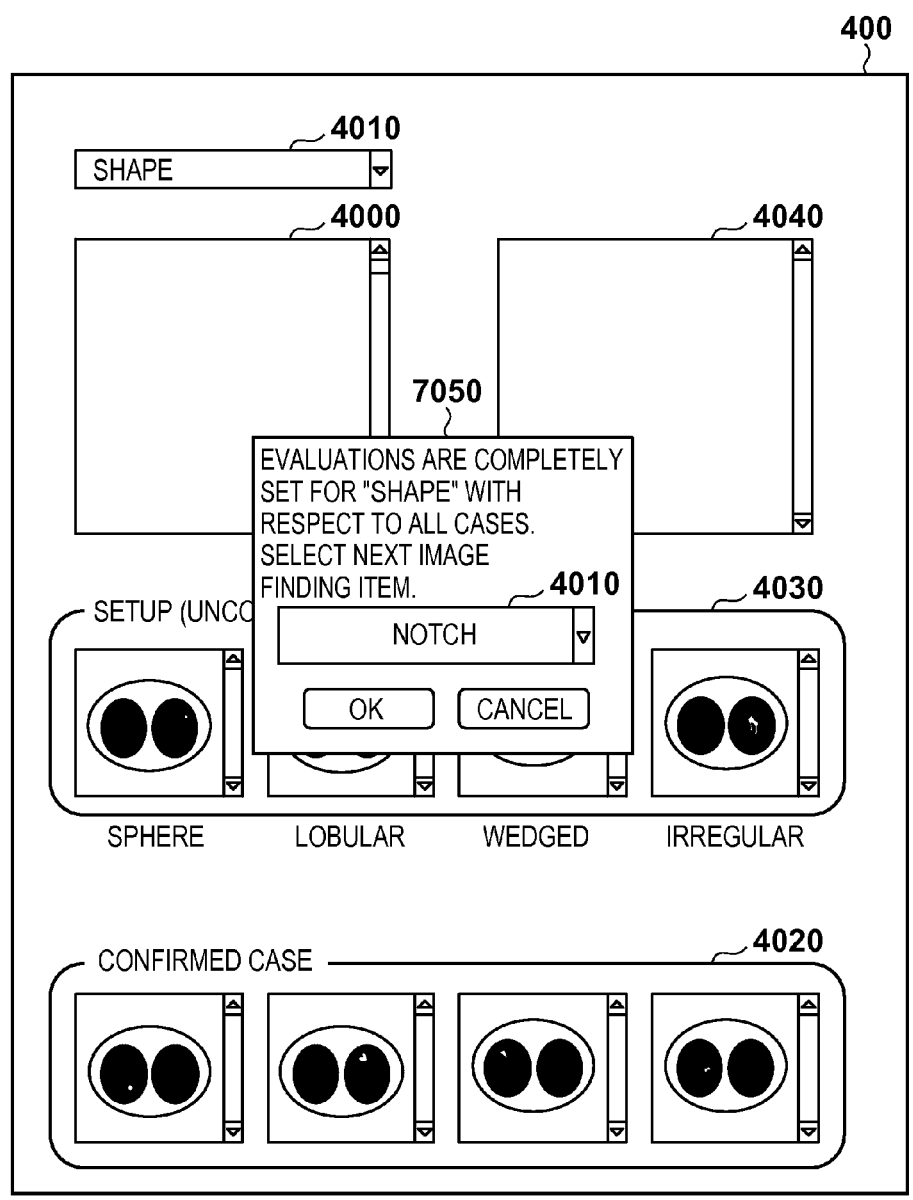
FIG. 7 is a view showing an example of a dialog in the first embodiment.

FIG. 7 shows an example of the GUI 400 when all cases have been evaluated with respect to a given image finding item (form). In this example, a selection dialog 7050 for selecting the next image finding item is displayed to prompt the user to perform the processing in step S3005. In this case, if the user presses the "Yes" button, the image finding item designated in the image finding item list 4010 is selected. If, for example, the user selects "notch", the processing in steps S3005 to S3014 is executed to display a screen like that shown in FIG. 8. FIG. 8 is a view showing another example of the GUI 400 in this embodiment.

In step S3050, the structured report creation unit 114 creates a structured report based on the evaluation for each image finding item stored in step S3025. More specifically, the structured report creation unit 114 creates a structured report based on the evaluation set in step S3025 for each image finding item with respect to each uninterpreted case obtained in step S3000. The created structured report is output to the case database 200 and stored.

According to this embodiment, it is possible to obtain the data group of target cases as uninterpreted cases and collectively set evaluations for the respective image finding items with respect to a plurality of cases. In addition, since it is possible to perform radiographic interpretation while comparing evaluations for each image finding item with reference to assigned cases and confirmed cases, the user can perform accurate radiographic interpretation when he/she is unsure about his/her determination. In addition, it is possible to create a structured report based on evaluations for set image finding items. This makes it possible to perform radiographic interpretation while comparing a plurality of cases for each image finding item. It is therefore possible to perform radiographic interpretation with less differences between cases.

[First Modification]

In this embodiment, in step S3000, the data group of uninterpreted cases and the data group of confirmed cases are obtained, and the data group of uninterpreted cases is stored in the target case list 4000. In addition, in step S3010, the confirmed case group is displayed in the confirmed case area 4020. However, other methods may be used. For example, the data group of cases for which only evaluations for some image finding items have been set may be obtained and stored in the target case list 4000. Alternatively, the user who uses the diagnosis support apparatus 100 may obtain an interpreted case group, and another use may obtain an interpreted case group. In this case, the other doctor can store the interpreted case group in the target case list 4000, and the user who uses the diagnosis support apparatus 100 can display the interpreted case group in the confirmed case area 4020. In addition, if the evaluation for the image finding item set in step S3020 differs from the evaluation for the original structured report attached to the case, a warning may be output. Alternatively, when a structured report is created in step S3050, the report may be created to allow discrimination between the evaluation in the original structured report and the newly attached evaluation.

[Second Modification]

In this embodiment, a representative image is set by using the abnormal shadow detection unit (not shown) in step S3000. However, this representative image need not always be fixed. For example, an axial image at the time of setting a VOI by using the medical image interpretation viewer in step S3015 or a tomogram image seen for the last time may be set as a representative image.

[Third Modification]

Figure 9:
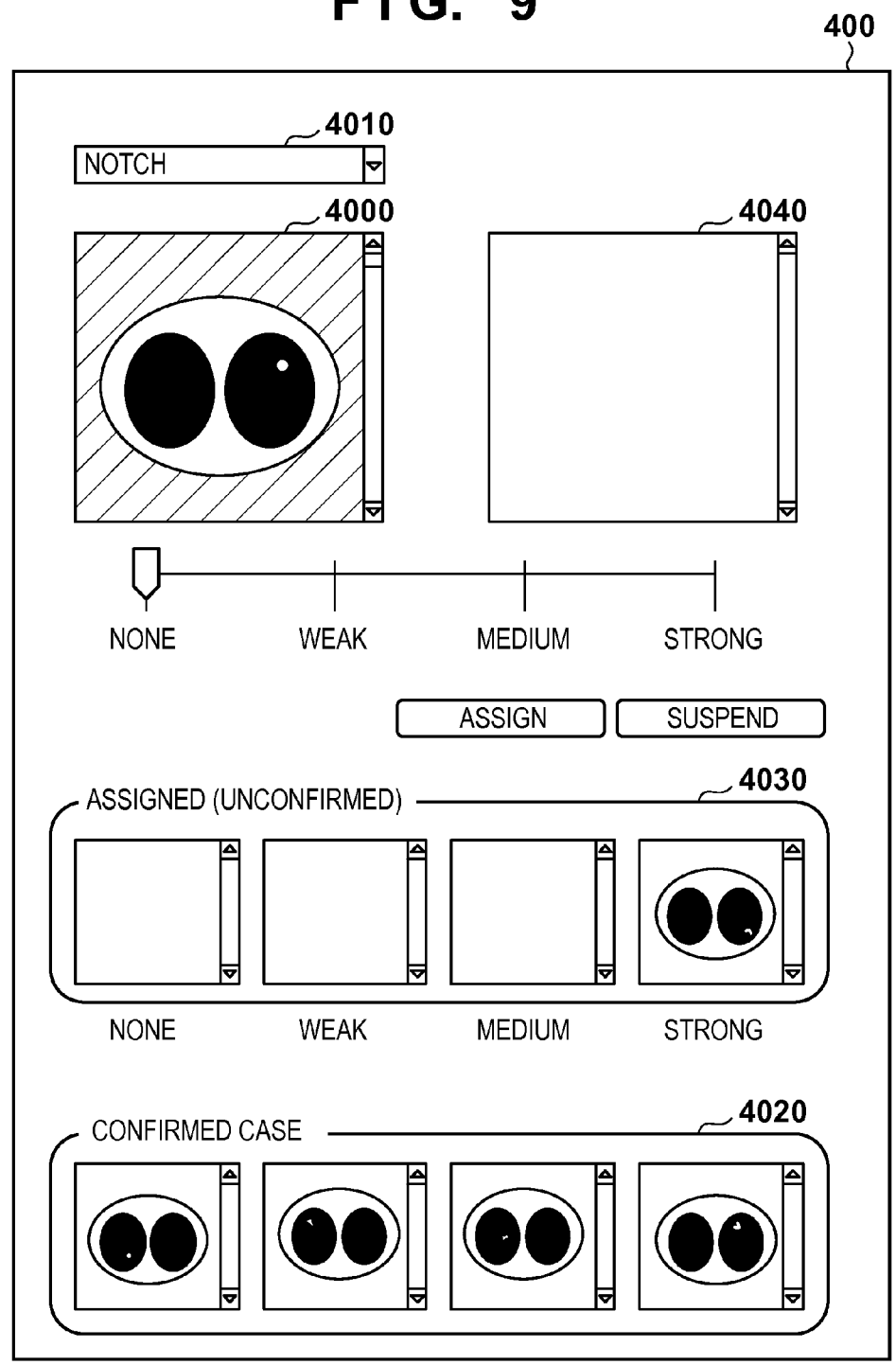
FIG. 9 is a view showing an example of a method of assigning evaluations in the first embodiment.

In this embodiment, in step S3020, the user sets an evaluation by dragging & dropping the case selected in step S3015 or S3035 to the assigned case area 4030. Alternatively, the user determines the selected case later by dragging & dropping the case to the evacuation case list 4040. However, the user may set an evaluation by another method and perform determination later. For example, the user may set an evaluation by using a slider bar like that shown in FIG. 9. In this example, the user determines an evaluation for a selected case by using the indicated slide bar and presses the set button, thereby setting an evaluation for an image finding item. When the user presses the set button, the selected case is stored in a list corresponding to the assigned case area 4030. On the other hand, when the user presses a suspense button, the selected case is stored in the evacuation case list 4040.

[Fourth Modification]

In this embodiment, in step S3045, the selection dialog 7050 for selecting the next image finding item is displayed to prompt the doctor to perform processing in step S3005. However, other methods may be used. For example, the diagnosis support apparatus 100 may automatically select an image finding item at the head of the image finding item list 4010. In addition, in the embodiment, when it it is determined in step S3045 that there is an image finding item for which no evaluation has been set, the processing in step S3005 is performed again. However, the processing in step S3005 may be performed at any timing. In this case, if the state has been temporarily stored in step S3027, when an image finding item is selected again, the set state is restored. In addition, the diagnosis support apparatus 100 may be configured to set the storage unit 118 as a database (not shown) at the time of the end of the diagnosis support apparatus 100 and read information from the database (not shown) into the storage unit 118 at the time of startup.

[Fifth Modification]

In this embodiment, when evaluations are set for all image finding items with respect to all interpretation target cases, a structured report is created in step S3050. However, other methods may be used. For example, a structured report may be created when evaluations are set for the image finding item selected in step S3005 with respect to all interpretation target cases in step S3040. In this case, data may be added to the report every time processing in step S3040 is performed. Furthermore, when an evaluation is set for an image finding item in step S3020, a structured report may be created concerning the case selected in step S3015. Likewise, a structured report may be created concerning the case selected in step S3035. In this case, re-set evaluations may be overwritten and stored or separately stored.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-148830, filed Jul. 17, 2013 which is hereby incorporated by reference herein in its entirety.

What is claimed is:

1. A diagnosis support apparatus to reduce differences in radiographic interpretation by collectively performing a plurality of radiographic interpretations, comprising:

at least one processor; and a memory having stored thereon instructions which, when executed by the at least one processor, cause the diagnosis support apparatus to:

obtain a plurality of target images as interpretation targets;

select a first image finding item of a plurality of image finding items;

sequentially assign an evaluation for the first image finding item to each image of the plurality of target images in accordance with operations input by a user;

select a second image finding item of the plurality of image finding items, wherein the second image finding item is different from the first image finding item and the selection of the second image finding item is performed after the selection of the first image finding item;

sequentially assign another evaluation indicating a degree for the second image finding item to each image of the plurality of target images in accordance with other operations input by a user;

display an image of the plurality of target images for which another evaluation indicating the degree is assigned, in accordance with the operation input, in a display area, of a plurality of display areas corresponding to evaluations configured to be assigned for the second image finding item, and being arranged in order of intensity of the indicated degree for the second image finding item, which corresponds to the evaluation assigned for the target image;

create a structured report based on the evaluations corresponding to each image finding item; and store the structured report in a database.

2. The apparatus according to claim 1, wherein the execution of the instructions by the at least one processor further causes the diagnosis support apparatus to display at least one target image of the plurality of target images, for which no evaluation has been assigned, in a display area different from the plurality of display areas.

3. The apparatus according to claim 2, wherein the execution of the instructions by the at least one processor further causes the diagnosis support apparatus to:

display a display object which accepts an operation input for designating another evaluation concerning the second image finding item; and assign the designated evaluation for an image which is displayed and for which no evaluation has been assigned, in accordance with the designation of an evaluation via the display object.

4. The apparatus according to claim 2, wherein as an image, of the displayed plurality of target images, for which no evaluation has been assigned is moved to one of the plurality of display areas according to an operation input, the execution of the instructions by the at least one processor further causes the diagnosis support apparatus to assign, for the target image, an evaluation corresponding to the display area to which the target image has been moved.

5. The apparatus according to claim 1, wherein the execution of the instructions by the at least one processor further causes the diagnosis support apparatus to display an image corresponding to another evaluation for the second image finding item together with a target image, of the plurality of target images, for which no evaluation has been assigned.

6. The apparatus according to claim 1, wherein the execution of the instructions by the at least one processor further causes the diagnosis support apparatus to display a first target image, of the plurality of target images, for which no evaluation has been assigned, and display a second target image, of a plurality of target images for which no evaluation has been assigned, which is different from the first target image, in accordance with an evaluation assigned to the first target image.

7. The apparatus according to claim 1, wherein the execution of the instructions by the at least one processor further causes the diagnosis support apparatus to switch an image finding item in a selected state in accordance with an operation input.

8. The apparatus according to claim 1, wherein the execution of the instructions by the at least one processor further causes the diagnosis support apparatus to display, in accordance with selection of an image finding item, at least one image for which no evaluation concerning the image finding item has been assigned, and display at least one image for which an evaluation concerning the selected image finding item has been assigned in a display area corresponding to each evaluation concerning the selected image finding item.

9. The apparatus according to claim 1, wherein if there are a plurality of target images to be displayed in a display area corresponding to the assigned evaluation, the execution of the instructions by the at least one processor further causes the diagnosis support apparatus to display at least one of the plurality of target images to be displayed.

10. The apparatus according to claim 1, wherein as an evaluation is assigned for a selected image finding item concerning each of a plurality of target images, the execution of the instructions by the at least one processor further causes the diagnosis support apparatus to display a dialog configured to select another image finding item different from the selected image finding item.

11. A diagnosis support apparatus to reduce differences in radiographic interpretation by collectively performing a plurality of radiographic interpretations, comprising:
   at least one processor; and
   a memory having stored thereon instructions which, when executed by the at least one processor, cause the diagnosis support apparatus to:
      obtain a plurality of target images as interpretation targets;
      select a first image finding item of a plurality of image finding items;
      sequentially assign an evaluation for the first image finding item to each image of the plurality of target images in accordance with operations input by a user;
      select a second image finding item of the plurality of image finding items, wherein the second image finding item is different from the first image finding item and the selection of the second image finding item is performed after the selection of the first image finding item;
      sequentially assign another evaluation indicating a degree for the second image finding item to each image of the plurality of target images in accordance with other operations input by a user;
      separately display images of the plurality of target images for which evaluations indicating a degree are assigned, in accordance with the operation input, in display areas, of a plurality of display areas corresponding to evaluations configured to be assigned for the second image finding item, and the plurality of target images being arranged in order of an intensity of the degree for the second image finding item, based on the assigned evaluations;
      create a structured report based on the evaluations corresponding to each image finding item; and
      store the structured report in a database.

12. A diagnosis support method to reduce differences in radiographic interpretation by collectively performing a plurality of radiographic interpretations, comprising:
   obtaining a plurality of target images as interpretation targets;
   selecting a first image finding item of a plurality of image finding items;
   sequentially assigning an evaluation for the first image finding item to each image of the plurality of target images in accordance with operations input by a user;
   selecting a second image finding item of the plurality of image finding items, wherein the second image finding item is different from the first image finding item and the selection of the second image finding item is performed after the selection of the first image finding item;
   sequentially assigning another evaluation indicating a degree for the second image finding item to each image of the plurality of target images in accordance with other operations input by a user;
   displaying an image for which another evaluation indicating a degree is assigned, in accordance with the operation input, in a display area, of a plurality of display areas corresponding to evaluations configured to be assigned for the second image finding item, and being arranged in order of an intensity of the degree for the second image finding item, which corresponds to the evaluation assigned to the target image;
   creating a structured report based on the evaluations corresponding to each image finding item; and
   storing the structured report in a database.

13. A diagnosis support method to reduce differences in radiographic interpretation by collectively performing a plurality of radiographic interpretations, comprising:
   obtaining a plurality of target images as interpretation targets;
   selecting a first image finding item of a plurality of image finding items;
   sequentially assigning an evaluation for the first image finding item to each image of the plurality of target images in accordance with operations input by a user;
   selecting a second image finding item of the plurality of image finding items, wherein the second image finding item is different from the first image finding item and the selection of the second image finding item is performed after the selection of the first image finding item;
   sequentially assigning another evaluation indicating a degree for the second image finding item to each image of the plurality of target images in accordance with other operations input by a user;
   separately displaying images of the plurality of target images for which evaluations indicating a degree are assigned, in accordance with the operation input, in display areas, of a plurality of display areas corresponding to evaluations configured to be assigned for the second image finding item, and the plurality of target images being arranged in order of an intensity of the degree for the second image finding item, based on the assigned evaluations;
   creating a structured report based on the evaluations corresponding to each image finding item; and
   storing the structured report in a database.

14. A non-transitory computer-readable storage medium storing a computer program for controlling a computer to execute a diagnosis support method which reduces differences in radiographic interpretation by collectively performing a plurality of radiographic interpretations, the method comprising:
   obtaining a plurality of target images as interpretation targets;
   selecting a first image finding item of a plurality of image finding items;

sequentially assigning an evaluation for the first image finding item to each image of the plurality of target images in accordance with operations input by a user;

selecting a second image finding item of the plurality of image finding items, wherein the second image finding item is different from the first image finding item and the selection of the second image finding item is performed after the selection of the first image finding item;

sequentially assigning another evaluation indicating a degree for the second image finding item to each image of the plurality of target images in accordance with other operations input by a user;

displaying an image of the plurality of target images for which another evaluation indicating a degree is assigned, in accordance with the operation input, in a display area of a plurality of display areas corresponding to evaluations configured to be assigned for the second image finding item and the plurality of target images being arranged in order of intensity of the degree for the second image finding item, which corresponds to the evaluation assigned for the target image;

creating a structured report based on the evaluations corresponding to each image finding item; and storing the structured report in a database.

15. A non-transitory computer-readable storage medium storing a computer program for controlling a computer to execute a diagnosis support method which reduces differences in radiographic interpretation by collectively performing a plurality of radiographic interpretations, the method comprising:

obtaining a plurality of target images as interpretation targets;

selecting a first image finding item of a plurality of image finding items;

sequentially assigning a first evaluation for the first image finding item to each image of the plurality of target images in accordance with operations input by a user;

selecting a second image finding item of the plurality of image finding items, wherein the second image finding item is different from the first image finding item and the selection of the second image finding item is performed after the selection of the first image finding item;

sequentially assigning another evaluation indicating a degree for the second image finding item to each image of the plurality of target images in accordance with other operations input by a user;

separately displaying images of the plurality of target images for which evaluations indicating a degree are assigned, in accordance with the operation input, in display areas of a plurality of display areas corresponding to evaluations configured to be assigned for the second image finding item and the plurality of target images being arranged in order of an intensity of the degree for the second image finding item, based on the assigned evaluations;

creating a structured report based on the evaluations corresponding to each image finding item; and storing the structured report in a database.

16. A diagnosis support apparatus to reduce differences in radiographic interpretation by collectively performing a plurality of radiographic interpretations, comprising:

at least one processor; and a memory having stored thereon instructions which, when executed by the at least one processor, cause the diagnosis support apparatus to:

obtain a plurality of target images as interpretation targets;

select a first image finding item of a plurality of image finding items;

sequentially assign an evaluation for the first image finding item to each image of the plurality of target images in accordance with operations input by a user;

select a second image finding item of the plurality of image finding items, wherein the second image finding item is different from the first image finding item and the selection of the second image finding item is performed after the selection of the first image finding item;

sequentially assign another evaluation indicating a degree for the second image finding item to each image of the plurality of target images in accordance with other operations input by a user;

display an image of the plurality of target images for which another evaluation indicating the degree is assigned, in accordance with the operation input, in a display area, of a plurality of display areas corresponding to evaluations configured to be assigned for the second image finding item, and being arranged in order of intensity of the indicated degree for the second image finding item, which corresponds to the evaluation assigned for the target image; and write the target images and evaluations associated with the target images to a memory.

17. A diagnosis support method to reduce differences in radiographic interpretation by collectively performing a plurality of radiographic interpretations, comprising:

obtaining a plurality of target images as interpretation targets;

selecting a first image finding item of a plurality of image finding items;

sequentially assigning an evaluation for the first image finding item to each image of the plurality of target images in accordance with operations input by a user;

selecting a second image finding item of the plurality of image finding items, wherein the second image finding item is different from the first image finding item and the selection of the second image finding item is performed after the selection of the first image finding item;

sequentially assigning another evaluation indicating a degree for the second image finding item to each image of the plurality of target images in accordance with other operations input by a user;

displaying an image of the plurality of target images for which another evaluation indicating the degree is assigned, in accordance with the operation input, in a display area, of a plurality of display areas corresponding to evaluations configured to be assigned for the second image finding item, and being arranged in order of intensity of the indicated degree for the second image finding item, which corresponds to the evaluation assigned for the target image; and writing the target images and evaluations associated with the target images to a memory.

18. A diagnosis support apparatus to collectively perform a plurality of radiographic interpretations, comprising:

at least one processor; and a memory having stored thereon instructions which, when executed by the at least one processor, cause the diagnosis support apparatus to:

obtain a plurality of target images as interpretation targets;
select a first image finding item of a plurality of image finding items;
sequentially assign an evaluation for the first image finding item to each image of the plurality of target images in accordance with operations input by a user;
select a second image finding item of the plurality of image finding items, wherein the second image finding item is different from the first image finding item and the selection of the second image finding item is performed after the selection of the first image finding item;
sequentially assign another evaluation indicating a degree for the second image finding item to each image of the plurality of target images in accordance with other operations input by a user;
display an image of the plurality of target images for which another evaluation indicating the degree is assigned in a display area, of a plurality of display areas corresponding to evaluations configured to be assigned for the second image finding item; and
write evaluations associated with the target images to a memory.

19. A diagnosis support method to collectively perform a plurality of radiographic interpretations, comprising:
obtaining a plurality of target images as interpretation targets;
receiving a first image finding item which is selected from a plurality of image finding items by a user;
sequentially assigning evaluations for the first image finding item to the plurality of target images in accordance with operations input by a user, wherein an evaluation for the first image finding item is assigned to a target image;
receiving a second image finding item which is selected from the plurality of image finding items by a user, wherein the second image finding item is different from the first image finding item and the selection of the second image finding item is performed after the selection of the first image finding item;
sequentially assigning evaluations for the second image finding item to each image of the plurality of target images in accordance with other operations input by a user wherein an evaluation for the second image finding item is assigned to a target image;
displaying an image of the plurality of target images for which an evaluation for the second image finding item is assigned in a display area, of a plurality of display areas corresponding to evaluations configured to be assigned for the second image finding item; and
writing evaluations associated with the target images to a memory.

* * * * *